United States Patent [19]

Heywang et al.

[11] Patent Number: 5,180,837
[45] Date of Patent: Jan. 19, 1993

[54] PILOSININE DERIVATIVES

[75] Inventors: Ulrich Heywang, Darmstadt; Michael Casutt, Heppenheim; Michael Schwarz, Gross-Gerau, all of Fed. Rep. of Germany

[73] Assignee: Merck Patent Gesellschaft mit beschraenkter Haftung, Darmstadt, Fed. Rep. of Germany

[21] Appl. No.: 781,608

[22] Filed: Oct. 23, 1991

[30] Foreign Application Priority Data

Oct. 23, 1990 [DE] Fed. Rep. of Germany ....... 4033612

[51] Int. Cl.$^5$ ................. C07D 233/64; C07D 405/06; A61K 31/415
[52] U.S. Cl. .............................. 548/315.4; 548/342.1
[58] Field of Search ............................. 548/336, 342

[56] References Cited

U.S. PATENT DOCUMENTS 4,220,654 9/1980 Bolhofer et al. ................. 548/336

FOREIGN PATENT DOCUMENTS 2182327 5/1987 United Kingdom .

OTHER PUBLICATIONS

Link et al., Helv. Chem. Acta 55, 1053 (1972).
The Merck Index; entry No. 1596, Eleventh Edition, 1989.

Primary Examiner—Mary C. Lee
Assistant Examiner—Lenora Ava Miltenberger
Attorney, Agent, or Firm—Millen, White, Zelano and Branigan

[57] ABSTRACT

The invention relates to a process for the preparation of racemic pilosinine derivatives as precursor for the alkaloid pilocarpine of pharmacological importance from a 5-formyl-1-alkylimidazole of the formula I

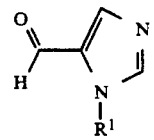

in which
$R^1$ is a straight-chain or branched alkyl chain with 1-6 C atoms which, via the stage of the thioacetal, is added onto γ-crotonolactone.

6 Claims, No Drawings

PILOSININE DERIVATIVES

SUMMARY OF THE INVENTION

The invention relates to a process for the preparation of racemic pilosinine derivatives from a 5-formyl-1-alkylimidazole of the formula I

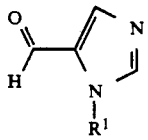

in which
R$^1$ is a low molecular weight straight-chain or branched alkyl chain with 1-6 C atoms.

Of particular interest is the derivative wherein R$^1$ is methyl, which represents a precursor of pilocarpine and can be converted into the latter in a known manner. Other pilosinine derivatives are valuable intermediates for the preparation of other target compounds. The products of the process of the invention can be routinely converted into one another using conventional chemistry.

Pilocarpine, an imidazole alkaloid, is the subject of numerous investigations because of its diverse pharmacological properties. Its outstanding pharmacological actions are diaphoretic effects, stimulation of the parasympathetic system, miotic actions and, especially, uses in ophthalmology.

Processes for the preparation of racemic and optically active pilocarpine are known. However, all these processes have a comparatively large number of synthetic steps which result in only low overall yields.

The synthesis of H. Link and K. Bernauer (Helv. Chem. Acta 55, 1053 (1972)) uses racemic pilosinine as precursor of pilocarpine. The starting material employed was 5-formyl-1-methylimidazole which can be obtained easily in a few steps from sarcosine. The process of Link and Bernauer comprises Stobbe condensation of an imidazole derivative with succinic diester to give a maleic monoester, the regioselective reduction thereof to form a butenolide from which pilosinine is derived by catalytic reduction in the last step.

The disadvantage of this process is that the Stobbe condensation takes place poorly and achieves maximum yields of 20%.

An object of the present invention is to find a process for the preparation of pilosinine derivatives for pilocarpine synthesis from readily obtainable starting materials, which takes place with high yields and substantially without byproducts.

This object has surprisingly been achieved by the process according to the invention by introducing an aldehyde protective group in the 5-formyl-1-alkylimidazole, followed by γ-lactenone addition.

Upon further study of the specification and appended claims, further objects and advantages of this invention will become apparent to those skilled in the art.

The invention therefore relates to a process for the preparation of the pilocarpine precursor pilosinine or derivatives thereof, characterized in that a) 5-formyl-1-alkylimidazoles of the formula I

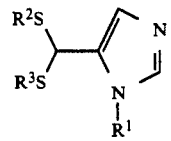

in which
R$^1$ is a low molecular weight straight-chain or branched alkyl chain with 1-6 C atoms
are converted into a thioacetal of the formula II

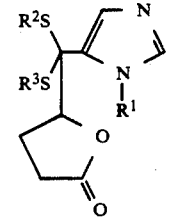

in which
R$^1$ has the stated meaning,
R$^2$ and R$^3$ are each, identically or independently of one another, a low molecular weight alkyl group with 1-5 C atoms, substituted or unsubstituted phenyl or benzyl or together are an alkylene group with 1-5 C atoms, b) the thioacetal of the formula II obtained in this way is deprotonated in the presence of a base and reacted with γ-crotonolactone to give a compound of the formula III

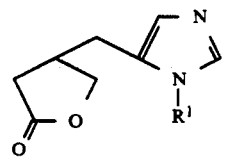

in which
R$^1$, R$^2$ and R$^3$ have the stated meaning,
c) the compound III obtained in this way is reduced to pilosinine derivatives of the formula IV

IV in which
R$^1$ has the stated meaning.

The compounds of the general formulae II and III are new and thus the present invention likewise relates to them.

If R$^1$, R$^2$ and R$^3$ are an alkyl radical, it can be straight-chain or branched.

Branched groups usually contain no more than two chain branchings. Preferred branched radicals are isopropyl, 2-butyl (1-methylpropyl), isobutyl (2-methylpropyl), 2-methylbutyl, isopenyl (3-methylbutyl), 2-methylpentyl or 3-methylpentyl.

$R^2$ and $R^3$ are preferably straight-chain having 1, 2, 3, 4 or 5 C atoms and are accordingly preferably methyl, ethyl, propyl, butyl, pentyl or hexyl.

$R^1$ is preferably methyl or ethyl.

If $R^2$ and $R^3$ are substituted phenylene or benzylene radicals, then they are preferably substituted by fluorine, chlorine, bromine, alkyl or alkoxy having up to 1-3 C atoms. In the case of monosubstitution, the substituent is preferable in o- or p-position relative to sulfur.

Starting from 5-formyl-1-alkylimidazole, which is easily obtained from the corresponding methyl alkylimidazole-5-carboxylates by reduction with lithium aluminum hydride followed by oxidation with active manganese dioxide (EP 0 336 250), firstly a protective group for the aldehyde functionality is introduced.

Suitable protective groups are those which are inert to strong bases but can easily and selectively be eliminated by complex reducing agents. The protective group is introduced as adequately disclosed in the literature by reacting the 5-formyl-1-alkylimidazole of the formula I with substituted or unsubstituted thiophenols, alkanethiols or alkenethiols under reflux. The reactants are preferably reacted in a suitable solvent with the addition of more than one equivalent of p-toluenesulfonic acid. Examples of suitable solvents are aromatic hydrocarbons such as benzene, xylene and toluene.

The deprotonation of the thioacetal in the following step is carried out in the presence of a base. Organic alkali metal compounds such as methyllithium, n-butyllithium, t-butyllithium and phenyllithium, and amides such as sodamide and lithium diisopropylamide, are suitable. The solvents which are employed are preferably hydrocarbons such as pentane, hexane, cyclohexane or ethers such as tetrahydrofuran, dioxane, tert.butylmethylether, diethylether or mixtures of suitable solvents. The reaction temperatures are expediently appropriate for the reactivity of the base employed and are between $-90°$ and $-50°$ C. The Michael addition to the $\gamma$-lactenone is carried out in situ in the same solvent or solvent mixture as the deprotonation reaction.

The methods for eliminating the protective group in the subsequent synthetic step depend on the nature of the radicals $R^2$ and $R^3$.

Complex metal hydrides are preferably employed, such as lithium aluminum hydride, sodium borohydride, Raney nickel or stannyl hydrides, especially tributyltin hydride, in the presence of a radical initiator such as azoisobutyronitrile. Suitable solvents depend on the nature of the reducing agent and are water, alcohols such as methanol, ethanol, isopropanol, t-butanol and n-butanol, ethers such as tetrahydrofuran, dioxane and diethyl ether, and hydrocarbons such as pentane, cyclohexane, hexane, benzene, toluene and xylene, or mixtures of the said solvents. The reaction temperature depends both on the metal hydride employed and on the solvent. However, the reactions are mostly carried out in the boiling range of the solvent.

The pilosinine derivatives of the formula IV are converted into pilocarpine derivatives in a known manner, usually by treating the pilosinine derivative with ethyl acetate and potassium t-butylate. The hydrogenation to the alcohols and the conversion thereof into the acetates are followed by pyrolysis to the olefins which, in the last step, are hydrogenated on a platinum catalyst.

The process according to the invention thus makes it possible to prepare pilocarpine and its derivatives from pilosinine derivatives in a straight forward manner and in high yields from easily obtainable starting materials in a few synthetic steps, some of which can be carried out in situ, and thus represents a considerable advance in the area of pilocarpine synthesis.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany P 40 33 612.3, filed Oct. 23, 1990, are hereby incorporated by reference.

EXAMPLES

Example 1

5-Dithiophenylmethyl-1-methylimidazole 33.0 g (300 mmol) of 5-formyl-1-methylimidazole are dissolved in 480 ml of toluene, and 68.5 g (360 mmol) of 4-toluenesulfonic acid monohydrate are added. After addition of 66.1 g (600 mmol) of thiophenol, the suspension obtained in this way is boiled under reflux with a water trap. The two-phase mixture obtained in this way is washed several times with 4N sodium hydroxide solution. The organic phase is dried over sodium sulfate and subsequently concentrated in vacuo. The residue obtained is 86.8 g (278 mmol, 93%) of 5-dithiophenylmethyl-1-methylimidazole as a slightly yellowish powder of melting point 78.5°–80°.

Example 2

5-(1,3-Dithian-2-yl)-1-methylimidazole 8.3 g (75.4 mmol) of 5-formyl-1-methylimidazole are dissolved in 120 ml of toluene, and 17.1 g (89.9 mmol) of 4-toluenesulfonic acid monohydrate are added. After addition of 8.12 g (75.0 mmol) of 1,3-propanedithiol, the suspension obtained in this way is boiled under reflux with a water trap. It is subsequently washed with 4N sodium hydroxide solution, and the organic phase is dried over sodium sulfate and concentrated in vacuo until crystallization starts. After storage in a refrigerator overnight, 9.6 g (47.9 mmol, 64%) of 5-(1,3-dithian-2-yl)-1-methylimidazole are obtained as a white solid of melting point 111.5°–112.5° C.

Example 3

3-(1-Methylimidazol-5-yl(dithiophenyl)methyl) butyrolactone 16.4 g (52.5 mmol) of 5-dithiophenylmethyl-1-methylimidazole are dissolved in 240 ml of tetrahydrofuran and cooled to $-78°$ C. 52.5 mmol of n-BuLi in 32 ml of hexane are added dropwise to this. After 30 minutes at $-78°$ C., 4.9 ml (69.8 mmol) of $\gamma$-crotonolactone are added and, after a further 1.5 hours, 250 ml of water are added dropwise while cooling in dry ice, and the mixture is allowed to warm to room temperature. It is then washed with ethyl acetate, acidified with glacial acetic acid and again extracted with ethyl acetate. The organic phase is dried over magnesium sulfate and concentrated in vacuo. The residue obtained in this way (13.8 g) is chromatographed on silica gel with dichloromethane/methanol (9:1). 6.6 g (16.6 mmol, 32%) of 3-(1-methylimidazol-5-yl-(dithiophenyl)methyl-butyrolactone are obtained as a white powder of melting point 80° C.

Example 4

3-(2-(1-Methylimidazol-5-yl)-1,3-dithian-2-yl)butyrolactone 6.9 g (40 mmol) of 5-(1,3-dithian-2-yl)-1-methylimidazole are dissolved in 190 ml of tetrahydrofuran and cooled to −78° C. 40 mmol of n-BuLi in 24 ml of hexane are added dropwise to this and, after 30 minutes, at −78° C., 3.8 ml (54 mmol) of γ-crotonolactone are added. After a further 1.5 hours at −78° C., 190 ml of water are added dropwise, and the mixture is warmed to room temperature. It is subsequently acidified with glacial acetic acid, the organic layer is separated off, and the aqueous phase is washed several times with ethyl acetate. The combined organic extracts are dried over magnesium sulfate and subsequently concentrated in vacuo. The residue is chromatographed on silica gel with dichloromethane/methanol (9:1). 3.1 g (10.9 mmol, 27%) of 3-(2-(1-methylimidazol-5-yl)-1,3-dithian-2-yl)butyrolactone are obtained as a yellow oil in this way.

Example 5

Pilosinine 3.5 g (9 mmol) of 3-(1-methylimidazol-5-yl)dithiophenylmethyl)butyrolactone are taken up in 500 ml of ethanol, and 15 g of freshly prepared Raney nickel are added and the mixture is boiled under reflux for 3.5 hours. The resulting suspension is filtered with suction through a layer of kieselguhr, and the filtrate is concentrated in vacuo. The residue is 0.8 g (4.4 mmol, 49%) of pilosinine.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound which is a thioacetal of the formula II

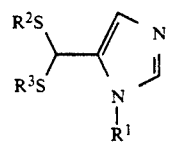

wherein
$R^1$ is a straight-chain or branched alkyl chain with 1-6 C atoms,
$R^2$ and $R^3$ are each, identically or independently of one another, a low molecular weight alkyl group with 1-5 C atoms, phenylene or benzylene radicals optionally substituted by fluorine, chlorine, bromine, alkyl or alkoxy having up to 1-3 C atoms.

2. A compound which is a butyrolactone of the formula III

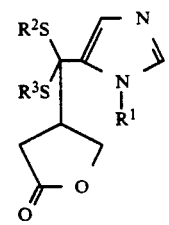

wherein
$R^1$ is a straight chain or branched alkyl chain with 1-6 C atoms,
$R^2$ and $R^3$ are each, identically or independently of one another, an alkyl group with 1-5 C atoms, phenylene or benzylene radicals optionally substituted by fluorine, chlorine, bromine, alkyl or alkoxy having up to 1-3 C atoms.

3. A compound according to claim 1, wherein $R^1$ represents a methyl radical.

4. A compound according to claim 1 wherein $R^1$ represents a ethyl radical.

5. A compound according to claim 1, wherein $R^2$ and $R^3$ each represent a straight-chain alkyl radical having 1, 2, 3, 4 or 5 C atoms.

6. A compound according to claim 1, wherein $R^2$ and $R^3$ represent a mono-substituted phenylene or benzylene radical, wherein the substituent is in o- or p-position relative to sulfur.

* * * * *

UNITED STATES PATENT AND TRADEMARK OFFICE
CERTIFICATE OF CORRECTION

PATENT NO. : 5,180,837
DATED : January 19, 1993
INVENTOR(S) : Ulrich HEYWANG et al.

It is certified that error appears in the above-identified patent and that said Letters Patent is hereby corrected as shown below:

Column 2, Line 35-42;   Please correct formula III to read:

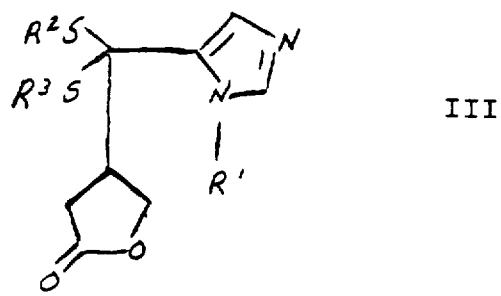

III

Signed and Sealed this

Seventh Day of December, 1993

*Attest:*

BRUCE LEHMAN

*Attesting Officer*   Commissioner of Patents and Trademarks